United States Patent [19]

Johnson

[11] Patent Number: 4,982,089

[45] Date of Patent: Jan. 1, 1991

[54] METHOD FOR OBTAINING THE SPECTRA OF AN UNSTABLE PRODUCT

[75] Inventor: Robert A. Johnson, Columbia, S.C.

[73] Assignee: The United States of America as represented by the Secretary of the Army, Washington, D.C.

[21] Appl. No.: 487,512

[22] Filed: Feb. 28, 1990

[51] Int. Cl.$^5$ .................... G01N 30/30; G01N 30/00
[52] U.S. Cl. .................... 250/304; 250/288; 250/339; 250/343; 73/23.37; 73/23.35
[58] Field of Search .............. 250/288, 304, 343, 339; 73/23.25, 23.35, 23.37, 23.39, 23.41

[56] References Cited

U.S. PATENT DOCUMENTS

| 4,245,494 | 1/1981 | Legewdre et al. | 73/19.02 |
| 4,432,225 | 2/1984 | Hayes et al. | 73/23.25 |
| 4,440,013 | 4/1984 | Adams | 73/23.37 |
| 4,764,676 | 8/1988 | Doyle | 250/353 |
| 4,883,958 | 11/1989 | Vestal | 250/288 |

Primary Examiner—Constantine Hannaher
Assistant Examiner—Edward J. Glick
Attorney, Agent, or Firm—Freddie M. Bush; Robert L. Broad

[57] ABSTRACT

A method of obtaining the spectra of a product wherein the product is passed through a gas chromatograph in a stream of helium to separate the product into components, with the components then being passed through a spectrometer to obtain the spectra of the components. The components are chilled to a temperature below about minus 10 degrees Celsius and preferably below about minus 20 degrees Celsius to render the components stable and non-volatile.

2 Claims, 1 Drawing Sheet

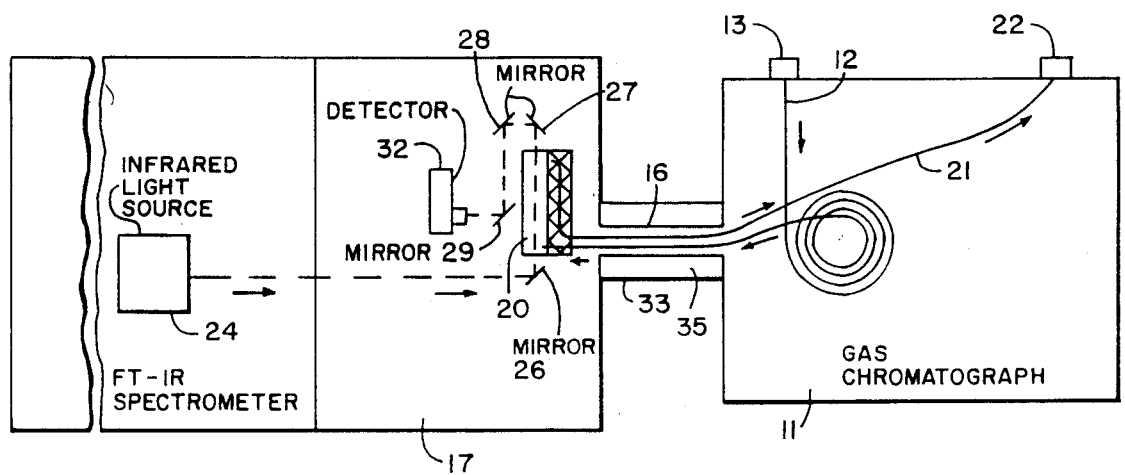

METHOD FOR OBTAINING THE SPECTRA OF AN UNSTABLE PRODUCT

DEDICATORY CLAUSE

The invention described herein may be manufactured, used, and licensed by or for the Government for governmental purposes without the payment to me of any royalties thereon.

BACKGROUND OF THE INVENTION

1. Field of the Invention

This invention relates to methods for obtaining the spectra of products.

2. Prior Art

It is known to obtain the spectra of a product by passing the product in a stream of helium through a gas chromatograph to separate the components of the product and then passing the components in series and at an elevated temperature through a Fourier transform infrared spectrometer to obtain the spectra of the components of the product. The components are heated to an elevated temperature during this process. The disadvantage of this process is that the spectra of volatile or unstable components cannot be obtained.

SUMMARY OF THE INVENTION

A process for obtaining the spectra of a product wherein the product is passed through a gas chromatograph in a stream of helium to separate the products into its components with the components being passed in series through a spectrometer to obtain the spectra of the components. The components pass through the spectrometer in a stream of helium and are chilled to a temperature below about −5 degrees Celsius.

DESCRIPTION OF THE DRAWING

The single FIGURE is a schematic drawing of the apparatus used for carrying out the process of the invention.

DETAILED DESCRIPTION OF THE INVENTION

Referring now in detail to the drawing, there is shown schematically a gas chromatograph 11 of a known type. The chromatograph 11 is provided with a first capillary tube 12 into which a product (not shown) is introduced through a port 13, a stream of helium also being introduced through the port 13 to carry the product through the first capillary tube 12.

The capillary tube 12 passes through a tube 16 which connects the chromatograph 11 to a spectrometer 17 of a known type and is connected to one end of a light pipe 20. A second capillary tube 21 leads from the other end of the light pipe back through the tube 16 to exit from the gas chromatograph 11 at an outlet port 22.

Infrared light from a source 24 in the spectrometer 17 is reflected off a first mirror 26 to pass through the light pipe 20 and the components passing through the light pipe. Light exiting from the light pipe 20 is reflected by mirrors 27, 28 and 29 to enter a detector 32 of a known type which detects and records the spectra of the components passing through the light pipe 20. The interior of the spectrometer 17 is maintained under a nitrogen purge to prevent the recording of the spectra of moisture, which would be present without the nitrogen purge.

A jacket 33 surrounds the tube 16 to provide a space 35 into which may be placed dry ice, liquid helium or some other cooling agent to chill the components passing through the capillary 12. A cooling jacket 37 is positioned in contact with the light pipe 20 to maintain the components at a lowered temperature. The jacket 37 may contain dry ice, liquid helium or some other chilling agent.

The chilling agent should be cold enough and in sufficiently close proximity to the capillary tube 12 to chill the components passing through this tube to a temperature no higher than about minus 10 degrees Celsius and preferably to a temperature no higher than minus 20 degrees Celsius. This chilling overcomes any tendency of the components to become volatile and stabilizes any components which might tend to disassociate into other components. Thus, this method allows one to obtain the infrared spectra of volatile and unstable products, which spectra is unobtainable by conventional methods.

EXAMPLE

A mixture of methoxymethanol and methanol was passed through the apparatus described above in a stream of helium. The mixture separated and infrared spectra showed two peaks, with the first being the excess methanol and the second being methoxymethanol. The methoxymethanol spectra showed no formaldehyde bands, indicating no decomposition of the methoxymethanol. In a conventional process the spectra for the methoxymethanol showed both methanol and formaldehyde bands.

What is claimed is:

1. A process for securing an infrared spectra of a volatile or unstable product, comprising
   a. passing the product in a gaseous form in a stream of helium through a gas chromatograph to separate different components of the product from each other,
   b. chilling the stream to a temperature to at least minus 10 degrees Celsius.
   c. passing the chilled stream through a Fourier transform infrared spectroscope to obtain the spectra of said components.

2. The method of claim 1 wherein the components are chilled to a temperature below about minus 20 degrees Celsius.

* * * * *